United States Patent [19]

Mormann et al.

[11] 4,009,152
[45] Feb. 22, 1977

[54] DIISOCYANATO-DIKETENES

[75] Inventors: Werner Mormann; Kuno Wagner, both of Leverkusen, Germany

[73] Assignee: Bayer Aktiengesellschaft, Leverkusen, Germany

[22] Filed: Aug. 22, 1975

[21] Appl. No.: 606,914

[30] Foreign Application Priority Data

Sept. 5, 1974 Germany .......................... 2442426

[52] U.S. Cl. .................... 260/77.5 AT; 260/75 NT; 260/343.9

[51] Int. Cl.$^2$ ................ C07D 305/12; C08G 18/06

[58] Field of Search ................ 260/343.9, 77.5 AT, 260/75 NT

[56] References Cited

UNITED STATES PATENTS

| 2,680,131 | 6/1954 | Gold | 260/77.5 ATX |
| 2,723,265 | 11/1955 | Stallmann | 260/77.5 AT X |
| 3,505,384 | 4/1970 | Krimm et al. | 260/77.5 AT X |

*Primary Examiner*—Melvyn I. Marquis
*Assistant Examiner*—S. M. Person
*Attorney, Agent, or Firm*—Gene Harsh; Joseph C. Gil

[57] ABSTRACT

The instant invention relates to novel diisocyanato-diketenes, i.e., compounds which contain the isocyanate and diketene groups of the β-lactone type in one molecule, and to a process for the production thereof.

6 Claims, No Drawings

DIISOCYANATO-DIKETENES

BACKGROUND OF THE INVENTION

It is known that diketenes may be obtained by allowing at least equimolar quantities of triethyl amine to act on carboxylic acid halides containing at least one hydrogen atom in the α-position to the chlorocarbonyl group. The monomeric ketenes formed in situ stabilize spontaneously to form dimers, trimers and polymers whose structure is governed both by the type and number of substituents on the α-carbon atom of the carboxylic acid chloride (J. Amer. Chem. Soc. 87 (1965), 5191).

Reactions of ketenes prepared in situ with isocyanates, in which malonimides are formed, are also known (J. Org. Chem. 30 (1965), 2466).

DESCRIPTION OF THE INVENTION

It has now been found that the reaction of isocyanato-carboxylic acid halides, unbranched in the α-position, with acid-binding agents gives diisocyanato-diketenes with a β-lactone structure in substantially quantitative yields.

It must be regarded as extremely surprising that there is virtually no reaction between the ketene and isocyanate group, instead diisocyanato-diketenes are formed in a uniform reaction. It is also surprising that the isocyanate groups do not undergo polymerization despite the presence of the basic acid-binding agent.

The present invention therefore relates to diisocyanato-diketenes corresponding to the following general formula:

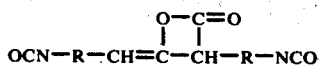

wherein
R represents a straight or branched chain aliphatic hydrocarbon radical with from 3 to 10 carbon atoms.

The invention also relates to a process for the production of diisocyanato-diketenes which comprises reacting isocyanato-carboxylic acid halides with an acid-binding agent at from −30° to +70° C, the reaction being accompanied by the liberation of hydrogen halide.

The novel compounds according to the invention represent particularly valuable starting compounds for the production of polyurethane plastics by the isocyanate polyaddition process. The diisocyanates represent trifunctional reactants for compounds containing isocyanate-reactive hydrogen atoms, such as polyhydroxyl compounds and/or polyamines known in polyurethane chemistry. This is so since, apart from the two isocyanate groups, the diketene group is also accessible to an addition reaction to form a keto-ester group or a keto-amide group.

The novel compounds are distinguished from conventional polyisocyanates by an almost ideal combination of desirable properties. Thus, the novel compounds have an extremely low vapor pressure at room temperature. They are odorless and physiologically safer than the diisocyanates known in polyurethane chemistry, such as diisocyanato-toluene isomers or hexamethylene diisocyanate. By virtue of their aliphatic character, the novel compounds may be used for the production of light-stable polyaddition products and, in this respect, are advantageously distinguished from conventional aromatic polyisocyanates. The novel compounds disclosed herein have a viscosity of from about 40 to about 100 cP at 20° C and, in this respect, are advantageously distinguished from the known aliphatic polyisocyanates with a reduced vapor pressure, for example tris(isocyanatohexyl)-biuret.

The present invention also relates to the use of the novel diisocyanato-diketenes disclosed herein as the isocyanate component in the production of polyurethane plastics by the isocyanate polyaddition process.

Starting materials suitable for use in the instant invention are isocyanato-carboxylic acid halides corresponding to the following general formula:

wherein
R represents a straight or branched-chain aliphatic hydrocarbon radical with from 3 to 10 carbon atoms; and
Hal represents a halogen atom, and preferably represents chlorine.

It is preferred to use isocyanato-carboxylic acid halides of the above formula in which there are 4 or more carbon atoms between the isocyanate group and the acid halide group.

The following are examples of suitable isocyanato-carboxylic acid halides: 5-isocyanato-valeric acid chloride, 5-isocyanato-azelaic acid chloride, 6-isocyanato-caproic acid chloride, 6-isocyanato-pelargonic acid chloride, 9-isocyanato-pelargonic acid chloride, 10-isocyanato-undecanoic acid chloride, 11-isocyanato-undecanoic acid chloride or 12-isocyanato-dodecanoic acid chloride. Isocyanato-carboxylic acid bromides such as 5-isocyanato-valeric acid bromide, 5-isocyanato-azelaic acid bromide, 6-isocyanato-caproic acid bromide, 6-isocyanato-pelagornic acid bromide, 9-isocyanato-pelagornic acid bromide 10-isocyanato-undecanoic acid bromide or 12-isocyanatodode-canoic acid bromide may also be used although the chlorides are preferred. It is, of course, also possible to use mixtures of different isocyanato-carboxylic acid halides.

Agents which liberate hydrogen chloride include: tertiary aliphatic and cycloaliphatic amines, such as triethyl amine, dimethyl benzyl amine, tributyl amine and N,N-dimethyl cyclohexyl amine. It is also possible to use tertiary amines which are bonded to a polymeric, insoluble carrier and which are known and generally commercially available as anion exchangers.

Examples of suitable solvents for use in the process according to the invention include acetone; benzene; toluene; xylenes; chlorinated hydrocarbons, such as dichloromethane, chloroform, carbon tetrachloride, 1,2-dichloroethane, chlorobenzene, dichlorobenzene and chlorotoluene; and ethers, such as diethyl ether, tetrahydrofuran and 1,4-dioxane; or mixtures of these solvents.

In a preferred embodiment of the process according to the invention, the isocyanato-carboxylic acid halide is dissolved in one of the aforementioned solvents, the tertiary amine is added dropwise at room temperature and, towards the end of the addition, the reaction mixture is briefly heated to elevated temperature in order to complete the reaction. However, it is, of course, also possible to initially introduce the acid-binding agent, optionally in solution, and to add the isocyanato-carboxylic acid halide dropwise.

Where the aforementioned solvents are used, the isocyanato-carboxylic acid chlorides used are preferably present in a concentration of from 0.1 to 2 mols per liter of solution.

The tertiary amine is preferably used in a stoichiometric quantity, i.e., 1 mol of amine per acid chloride group in the isocyanato-carboxylic acid chloride. It is also possible to use an excess of the amine without reducing the yield or giving rise to undesirable secondary reactions. However, the use of an excess of amine does not generally afford any advantages over the use of stoichiometric quantities.

The process according to the invention is preferably carried out at temperatures of from −30° to +70° C. The temperature prevailing during addition of the tertiary amine is generally from −30° to +40° C and is preferably from 0° to +25° C. Towards the end of the reaction, the reaction mixture is generally heated to from 50° to 70° C.

The reaction mixture is best worked-up by initially removing the hydrochloride of the tertiary amine from the reaction mixture by suction filtration. The solvent is then removed in vacuo. Any starting material present may be separated off by thin-layer distillation in vacuo or by extraction with an apolar solvent, such as cyclohexane.

The reaction products obtained are diisocyanato-diketenes corresponding to the following general formula:

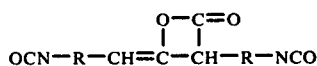

in which
R represents a straight or branched chain aliphatic hydrocarbon radical with from 3 to 10 carbon atoms.

The use of the preferred isocyanato-carboxylic acid halides, in which there are 4 or more carbon atoms between the acid chloride group and the isocyanate group, results in the formation of the preferred compounds according to the invention, in which there are 3 or more carbon atoms between the isocyanate groups and the diketene group.

It is of course also possible to modify the process according to the invention to the extent that isocyanato-carboxylic acid halides of the above general formula, wherein the radical R has inert substituents, such as chlorine or bromine atoms, alkoxy or cycloalkyl radicals, or wherein the radical R is interrupted by hetero atoms, such as oxygen or sulphur, are used as starting materials. The use of isocyanato-carboxylic acid halides with 3 carbon atoms between the isocyanate group and acid halide group, such as 4-isocyanato-butyric acid chloride, is also possible, but is less preferred.

The novel compounds according to the invention are yellowish, free-flowing liquids with viscosities of from about 40 to about 100 cP at 20° C. As already mentioned, their principal application is as isocyanate component in the production of polyurethane plastics.

The invention is further illustrated, but is not intended to be limited by the following examples, in which all parts and percentages are by weight unless otherwise specified.

EXAMPLE 1

177 g of freshly-distilled 6-isocyanato-caproic acid chloride and 1500 ml of anhydrous toluene are introduced into a three-necked flask equipped with a stirrer, internal thermometer and reflux condenser through which a gentle stream of dry nitrogen continuously flows. 101 g of triethyl amine are added dropwise to this solution, with vigorous stirring over a period of 1 hour. The temperature is maintained at about 20° C by cooling with cold water. The reaction mixture turns pale yellow in color and a deposit is immediately formed. After all the triethyl amine has been introduced, the reaction mixture is stirred for another hour at room temperature and then heated to 60° C for 15 minutes. After cooling to a temperature of 5° C with ice water, the triethyl amine hydrochloride is removed by suction filtration and washed twice with toluene, the amount of toluene used in each wash being 200 ml. The filtrate is concentrated in a water-jet vacuum and final traces of solvent removed by thin-layer distillation at 110° C/0.1 mm Hg. The diisocyanato-diketene is obtained in a yield of 125 g (90% of the theoretical yield), accumulating in the form of a clear, odorless, reddish-yellow liquid with a viscosity of 40 cP at 20° C.

$$\begin{array}{c} OCN-(CH_2)_4-CH=C=O \\ | \quad | \\ OCN-(CH_2)_4-HC-C=O \end{array}$$

NCO* calc: 45.3%   Found: 43.4%
Analysis:  Calc: C 60.4%   H 6.5%   N 10.1%
           Found: C 60.8%  H 6.75%  N 10.1%

IR:  1720 and 1870 cm⁻¹         γC=O
     2250 cm⁻¹                  γNCO

EXAMPLE 2

Following the procedure of Example 1, 245.5 g of 11-isocyanato-undecanoic acid chloride are reacted with 101 g of triethylamine in 2000 ml of xylene. An odorless, yellowish, free-flowing liquid with a viscosity of 37 cP at 20° C is obtained in a yield of 200 g (92% of the theoretical yield).

$$\begin{array}{c} OCN-(CH_2)_9-CH=C=O \\ | \quad | \\ OCN-(CH_2)_9-HC-C=O \end{array}$$

NCO* Calc: 30.1%        Found: 28.7%

IR:  1723 and 1865 cm⁻¹         γC=O
     2250 cm⁻¹                  γNCO

EXAMPLE 3

Following the procedure of Example 1, 45 g of 4-isocyanato-valeric acid chloride are reacted with 28 g of triethyl amine in 250 ml of toluene, giving 32 g (91% of the theoretical yield) of a reddish liquid with a viscosity of 95 cP at 20° C which contains the bands characteristic of the isocyanate and diketene group in the infra-red spectrum.

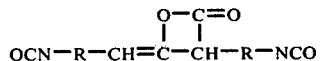

NCO* calc: 50.3%     Found 48.2%

EXAMPLE 4

Following the procedure of Example 1, 56 g of 11-isocyanato-dodecanoic acid chloride are reacted with 22 g of triethyl amine in 250 ml of toluene, giving 46.3 g (96% of the theoretical yield) of a pale yellow liquid with a viscosity of 43 cP at 20° C.

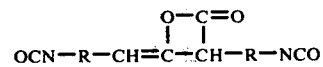

NCO* calc: 27.6%     Found: 26.9%

\* The diketene group also reacts when the NCO content is determined by titration with dibutyl amine/HCl. Accordingly, the actual NCO contents amount to approximately two thirds of the measured NCO contents indicated hereinbefore in Examples 1–4. The same is true with respect to the indicated calculated NCO-values. These values have been calculated assuming that the compounds are "pseudo-triisocyanates". In order to convert these calculated figures into the actual calculated NCO contents of the diisocyanates of Examples 1–4 all calculated values have to be multiplied with ⅔.

EXAMPLE 5

This Example demonstrates that the diisocyanato-diketenes according to the invention react with atmospheric moisture to form elastic films. 10g of the diisocyanato-diketene obtained in accordance with Example 2 are mixed with 1 drop of a zinc octoate solution and poured onto a glass plate. After 48 hours, an insoluble, clear elastic film is obtained.

EXAMPLE 6

50 g of a 65% solution of a branched polyester polyol (with an OH-content of 8%) in xylene;ethyl glycol acetate (1:1), are intensively mixed with 14.2 g of the diisocyanato-diketene obtained in accordance with Example 1. Films are cast on a glass substrate, forming a very hard elastic lacquer which is insoluble in the conventional solvents.

What is claimed is:

1. Diisocyanato-diketenes corresponding to the following general formula:

$$OCN-R-CH=\overset{\overset{\displaystyle O-C=O}{|\quad\quad|}}{C-CH}-R-NCO$$

wherein
R represents a straight or branched-chain aliphatic hydrocarbon radical with from 3 to 10 carbon atoms.

2. A process for the production of diisocyanato-diketenes comprising reacting isocyanato-carboxylic acid halides with an acid-binding agent at from −30° to +70° C, the reaction being accompanied by the liberation of hydrogen halide.

3. The process of claim 2, wherein said acid-binding agent is a tertiary aliphatic or cycloaliphatic amine.

4. The process of claim 3, wherein the reaction is conducted in the presence of an inert organic solvent.

5. The process of claim 4, wherein one mol of acid-binding agent is used per acid chloride group in the isocyanato-carboxylic acid halide.

6. In a process of producing a polyurethane by reacting an organic isocyanate with an active hydrogen containing compound, the improvement wherein the organic isocyanate is a diisocyanato-diketene corresponding to the following general formula $$OCN-R-CH=\overset{\overset{\displaystyle O-C=O}{|\quad\quad|}}{C-CH}-R-NCO$$

wherein
R represents a straight or branched-chain aliphatic hydrocarbon radical with from 3 to 10 carbon atoms.

* * * * *